(12) United States Patent
Patterson et al.

(10) Patent No.: US 8,307,478 B2
(45) Date of Patent: Nov. 13, 2012

(54) DISPOSABLE COMFORT SHEET

(75) Inventors: Richard A. Patterson, Georgetown, TX (US); Bryan D. Blackford, Cedar Park, TX (US)

(73) Assignee: MediGlider Corp., Austin, TX (US)

( * ) Notice: Subject to any disclaimer, the term of this patent is extended or adjusted under 35 U.S.C. 154(b) by 598 days.

(21) Appl. No.: 12/569,352

(22) Filed: Sep. 29, 2009

(65) Prior Publication Data
US 2011/0072582 A1    Mar. 31, 2011

(51) Int. Cl.
*A61G 7/10* (2006.01)
*A61G 7/14* (2006.01)

(52) U.S. Cl. ............... 5/487; 5/484; 5/81.1 C; 5/500; 5/907

(58) Field of Classification Search ............ 5/484, 487, 5/81.1 C, 81.1 HS, 488, 496, 500, 907; 604/361, 604/389, 356
See application file for complete search history.

(56) References Cited

U.S. PATENT DOCUMENTS

| | | | | |
|---|---|---|---|---|
| 3,654,059 | A * | 4/1972 | Zisblatt | 428/41.5 |
| 4,097,943 | A | 7/1978 | O'Connell | |
| 4,358,865 | A * | 11/1982 | Pagel et al. | 5/487 |
| 4,738,674 | A * | 4/1988 | Todd et al. | 604/361 |
| 4,840,841 | A * | 6/1989 | Madsen | 428/136 |
| 4,923,453 | A * | 5/1990 | Bullard, Jr. | 604/356 |
| 5,086,530 | A * | 2/1992 | Blake | 5/484 |
| 5,595,754 | A * | 1/1997 | Ito et al. | 424/443 |
| 5,850,642 | A | 12/1998 | Foster | |
| 6,349,432 | B1 | 2/2002 | Scordato et al. | |
| 7,159,257 | B1 * | 1/2007 | Struthers | 5/487 |
| 7,540,044 | B2 | 6/2009 | Patterson et al. | |
| 2003/0163870 | A1 * | 9/2003 | Porter et al. | 5/490 |
| 2004/0060112 | A1 | 4/2004 | Fell et al. | |
| 2004/0237235 | A1 | 12/2004 | Visioli et al. | |
| 2005/0055768 | A1 | 3/2005 | Assink | |
| 2009/0068633 | A1 | 3/2009 | Cohen et al. | |
| 2011/0152641 | A1 * | 6/2011 | Fernfors et al. | 600/309 |

\* cited by examiner

*Primary Examiner* — Michael Trettel
(74) *Attorney, Agent, or Firm* — Jack V. Musgrove

(57) ABSTRACT

A disposable comfort sheet has a waterproof layer and an absorbent layer, with adhesive strips applied to the waterproof layer along side edges. The sheet is adapted for use with a patient transfer device having upper and lower counter-rotating belts, and protects the upper belt against contamination. The patient transfer device may have registration marks for installation of the sheet, and indicator marks can be printed at predetermined locations on the waterproof layer for alignment with the registration marks. The sheet may include various means for indicating prior use by a patient, such as an ink pattern made of a heat-sensitive or moisture-sensitive ink. The sheet may further include a peel-away layer releasably bonded to the absorbent layer, with additional longitudinal adhesive strips applied to the side edges of the peel-away layer. The peel-away layer protects the lower belt against contamination from the sheet after a patient is delivered.

16 Claims, 8 Drawing Sheets

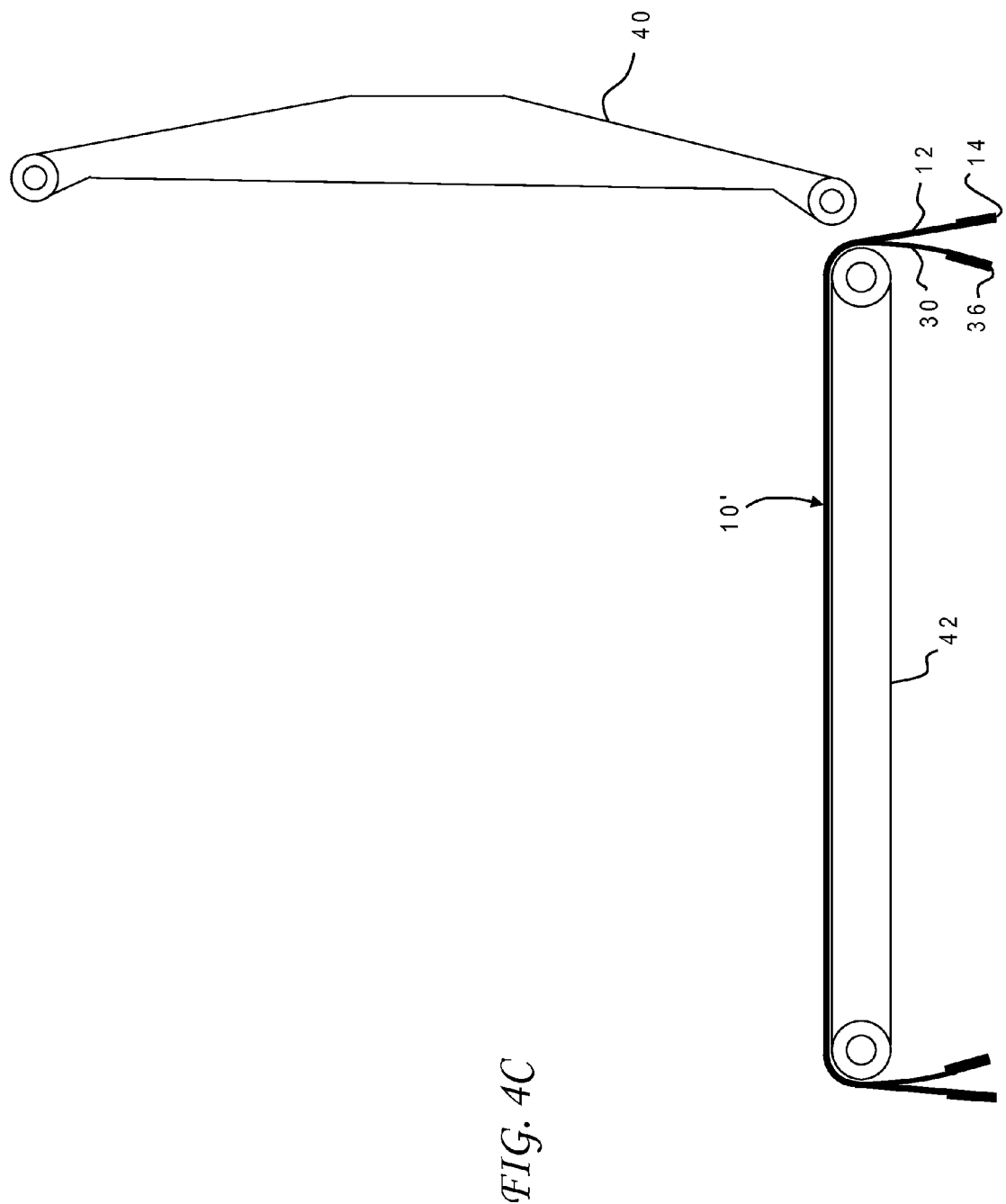

DISPOSABLE COMFORT SHEET

BACKGROUND OF THE INVENTION

1. Field of the Invention

The present invention generally relates to maintaining hygiene in a hospital-like setting, and more particularly to an article and method for reducing the contamination of surfaces of a patient transfer device.

2. Description of the Related Art

A wide variety of products have been designed to move objects from one location to another and, in particular, transfer mobility-impaired individuals such as patients. In a hospital setting, patients must often be transported from their beds to an examination table or operating table, and back again. Basic devices for transferring patients include stretchers that are carried manually by two attendants, and wheeled gurneys that can more easily be handled by a single attendant.

The patient transfer device developed by Patterson and Smucker (U.S. Pat. No. 7,540,044) is designed to make the action of patient transfer between two support surfaces easier. Two tables, upper and lower, have counter-rotating belts which acquire and deliver a patient laterally with "frictionless" engagement, requiring minimal effort on the part of the operator of the device.

Such patient transfer devices will inevitably become contaminated after repeated usage by the patients' bodily fluids such as blood, sweat, urine, or mucus. Hospitals in particular have a special duty to maintain the hygiene of their medical equipment, and therefore, must be continuously vigilant about keeping facilities sanitary. In regards to patient transfer devices, it is of great importance to keep the upper and lower belts free of contaminants which can easily transmit many diseases to patients and medical professionals operating the device.

Medical staff spend a significant amount of time and effort in cleaning medical equipment, therefore any solution to this problem of maintaining high levels of cleanliness would have to be practical and efficient. An operator of patient transfer devices, such as a nurse or medical assistant, would be best aided by a method which would reduce the amount of effort required to clean the device, as well as reducing the amount of time the operator would spend cleaning it.

One approach to reducing infectious transmission is to use a sheet-like protective material that temporarily resides on a belt as exemplified in U.S. Pat. No. 5,850,642. This sheet is designed to increase the hygiene of the patient transfer device by acting as a barrier between the actual patient and the upper belt on which the patient would be lying. The sheet may be made out of foam plastic, absorbent padding, or waterproof material. A single-width sheet is installed in the patient transfer device by first pivoting the upper table to an open (acute) position, and then inserting the sheet between the upper and lower tables. The upper table is then pivoted back to the closed position with the sheet resting between the two tables. The outer end portion of the sheet is wrapped around the end of the upper table and is held in place by means of a hook and loop attachment. The sheet is then able to rotate around with the upper belt as it rotates. In another embodiment the sheet is double-wide and is folded before being inserted between the upper and lower belts, and the two outer end portions of the sheet are respectively wrapped around the ends of the upper and lower belts.

While the '642 sheet provides some protection against contamination, it still possesses many disadvantages. It still requires some skill to install the sheet so that it is properly aligned both longitudinally and transversely. Additionally, if the sheet were completely made of absorbent material then it would not be waterproof and fluids might saturate an area of the sheet and permeate through to the bottom side. Conversely, if the sheet were completely made of waterproof plastic then it may not be able to sufficiently contain bodily fluids which could trickle off the edge of the sheet and contaminate either the patient transfer belts or the patient support surface.

One serious drawback of the double-wide (folded) sheet in the '642 patent is that when the patient is being delivered, the sheet cannot be recaptured between the upper and lower belts. This deficiency causes the sheet to gather and bunch at the side of the table, inevitably resulting in contamination of the patient transfer device and possibly other objects in the surrounding area. With either of the '642 embodiments, if the sheet is not visibly stained by bodily fluids even though it is contaminated by them from prior use, there may be no way for the operator of the patient transfer device to discern that the sheet has already been used. In such a case the operator may carelessly re-use the contaminated sheet, risking the spread of infection.

It would, therefore, be desirable to devise an improved construction for a disposable sheet to be used with a patient transfer device which could more effectively reduce infectious transmissions. It would be further advantageous if the improved sheet construction could increase patient comfort, or include material characteristics which would facilitate the physical acquisition and delivery of the patient.

SUMMARY OF THE INVENTION

It is therefore one object of the present invention to provide an improved disposable sheet for use with a patient transfer device.

It is another object of the present invention to provide such an improved disposable sheet which offers enhanced protection against infectious transmission leading to nosocomial infections by further reducing the possibility of contamination between uses of a patient transfer device.

It is yet another object of the present invention to provide such an improved disposable sheet which more readily allows the patient transfer device operator to determine that the sheet has already been used and should be discarded.

It is yet another object of the present invention to provide greater comfort for the patient by wicking and retaining body fluids away from the patient's skin.

The foregoing objects are achieved in a disposable comfort sheet having a seamless, waterproof layer and an absorbent layer, with a first longitudinal adhesive strip applied to the waterproof layer along a first side edge thereof, and a second longitudinal adhesive strip applied to the waterproof layer along a second side edge thereof opposite the first side edge. The adhesive strips are preferably covered with a liner that is easily removed prior to installation of the sheet onto one of the belts in the patient transfer device.

The absorbent layer may be directly bonded to the waterproof layer, and may further include a section having additional absorbency to retain higher amounts of fluids than the remainder of the absorbent layer. An antimicrobial agent may be applied to the absorbent layer. The adhesive strips preferably have a dual layer adhesive construction with a higher adhesion pressure-sensitive adhesive (PSA) bonded to the waterproof layer and a lower adhesion PSA laminated with the stronger PSA. The surface of the lower adhesion PSA will be in contact with and temporarily bonded to the surface of the patient transfer device belt when properly installed. The internal strength of the PSA layers is sufficiently high to prevent adhesive splitting or delamination which could cause adhesive residue on the belts.

Further, the internal bond between the waterproof and absorbent layers is high enough to prevent delamination of these layers as the sheet is removed from the patient transfer device belt. The various adhesion levels and internal strengths of the various layers in the comfort sheet and adhesive strips thereby provide a strong bond between the comfort sheet and the patient transfer device belt when in use, and allow a clean removal of the adhesive and comfort sheet from the belt (leaving no adhesive residue or fragments of comfort sheet) when the sheet is disposed of after use.

The disposable comfort sheet is particularly adapted for use with a patient transfer device having upper and lower counter-rotating belts. The patient transfer device may have registration marks for installation of the disposable comfort sheet, and indicator marks can be printed at predetermined locations on an outer surface of the waterproof layer for alignment with the registration marks.

The disposable comfort sheet may include various means for indicating use of the sheet by a patient. For example, an ink pattern can be formed on the absorbent layer, wherein the ink pattern is made with a heat-sensitive ink or a moisture-sensitive ink. The ink pattern could be invisible prior to patient use and visible after patient use, or could change from a first color prior to patient use to a second color after patient use.

The disposable comfort sheet may further include a peel-away layer releasably bonded to a side of the absorbent layer opposite the waterproof layer, with additional longitudinal adhesive strips applied to the side edges of the peel-away layer. The peel-away layer is also preferably waterproof. The peel-away layer can be releasably bonded to the absorbent layer by spot welding spread substantially across the entire area of the sheet.

The present disclosure also provides novel methods for installation and deployment of the various embodiments of the disposable comfort sheet.

The above as well as additional objectives, features, and advantages of the present invention will become apparent in the following detailed written description.

BRIEF DESCRIPTION OF THE DRAWINGS

The present invention may be better understood, and its numerous objects, features, and advantages made apparent to those skilled in the art by referencing the accompanying drawings.

FIGS. 4A-4F are front elevational views of the upper and lower belts of the patient transfer device of FIG. 3 in closed and open positions illustrating installation and deployment of a disposable comfort sheet constructed in accordance with the present invention.

The use of the same reference symbols in different drawings indicates similar or identical items.

DESCRIPTION OF THE PREFERRED EMBODIMENT(S)

Figure 1A:
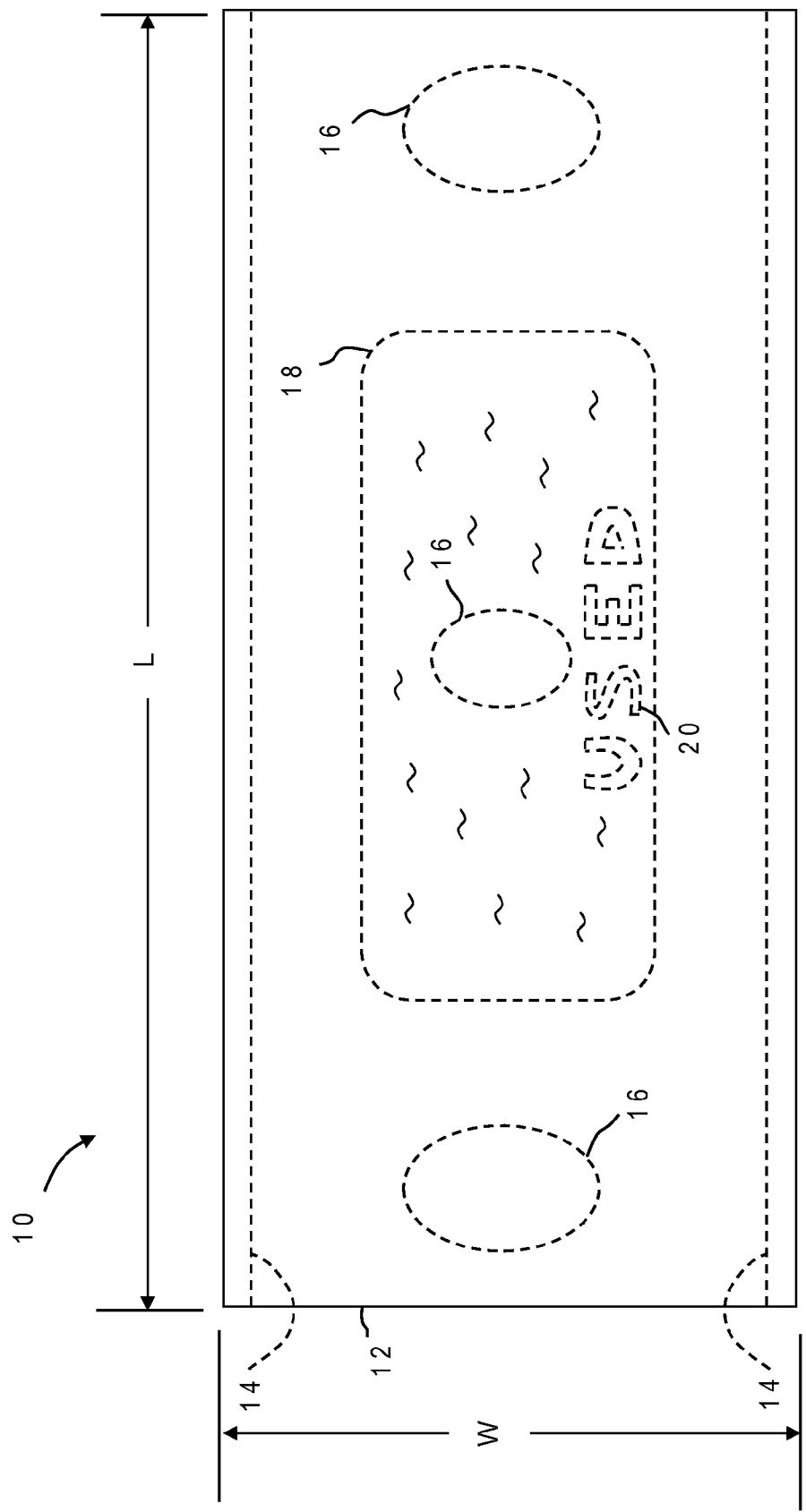
FIG. 1A is a top plan view of one embodiment of a disposable comfort sheet constructed in accordance with the present invention.
Figure 1B:
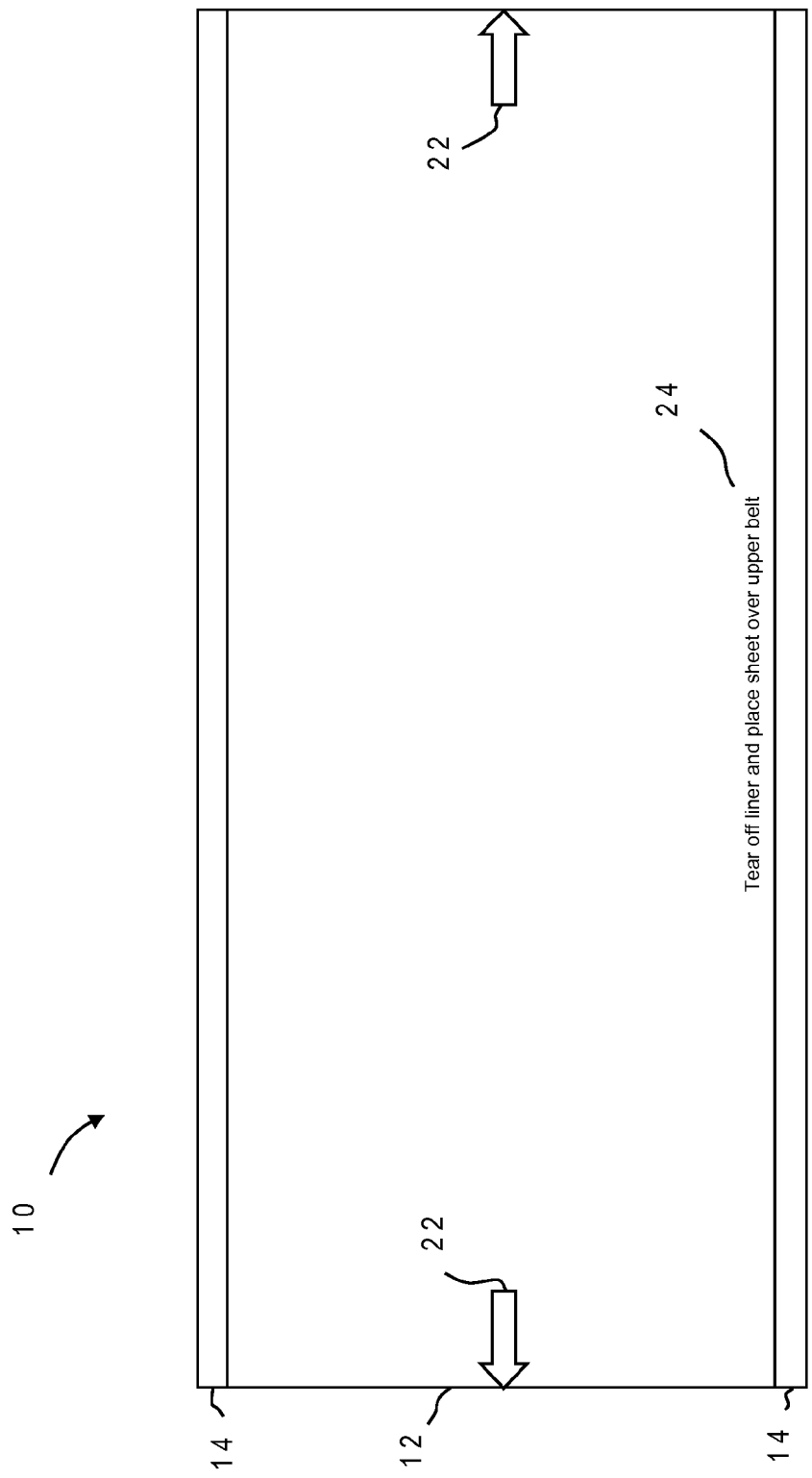
FIG. 1B is a bottom plan view of the disposable comfort sheet of FIG. 1A

With reference now to the figures, and in particular with reference to FIGS. 1A and 1B, there is depicted one embodiment of a disposable comfort sheet 10 constructed in accordance with the present invention. Disposable comfort sheet 10 is intended to be single-use only and will be disposed of, in most cases, after usage. Disposable comfort sheet 10 is generally comprised of a sheet-like protective barrier 12 and two adhesive strips 14.

In the depicted embodiment protective barrier 12 is rectangular in shape but will generally comport with the dimensions of the patient transfer device it is designed for as explained further below in conjunction with FIG. 3. The primary function of protective barrier 12 is to prevent contamination of the patient transfer device by a patient being transported, but it includes additional features adapted to increase patient comfort and simplify use. Some of these features are seen on the top side of sheet 10 as shown in FIG. 1A, while other features are seen on the bottom side of sheet 10 as shown in FIG. 1B.

Patient comfort features include multiple padding areas 16 located on the top of protective barrier 12, two of which are near the head and foot ends thereof "Head" and "foot" ends (or "front" and "back") as used herein are arbitrary because either end could correspond to a patient's head or feet depending on the orientation of the patient transfer device, so these terms should not be construed in a limiting sense.

An absorbent section 18 is characterized in this embodiment as a rounded rectangle located in the center of the top side of protective barrier 12. While the entire area of protective barrier 12 may provide some absorbency as explained further below, absorbent section 18 is designed to retain higher amounts of fluids. Another padding layer 16 lies within absorbent section 18. The specific number and location of the padding areas and the absorbent sections may vary considerably depending on the intended use.

In the preferred embodiment, the top side of protective barrier 12 is also provided with an ink pattern 20. Ink pattern 20 can be heat sensitive (so that it becomes visible after it has been exposed to heat from the patient), or it can be moisture sensitive (so that it becomes visible after it has been exposed to moisture from the patient), or can have other properties that indicate past usage of disposable comfort sheet 10, including mechanical features or materials indicating that significant pressure has been applied to the sheet. Instead of "invisible" ink, the ink may change from one color to another, such as blue prior to use, and red after use. The unused color may match a color of absorbent layer 12b. Ink pattern 20 could further be both heat- and moisture-sensitive, and could be formed using multiple inks. Suitable inks include for example microencapsulated thermochromic inks manufactured by Gem'innov of France (heat-sensitive) or the moisture activated inks manufactured by Stallion Impex of New Jersey (moisture-sensitive). In this embodiment, ink pattern 20 spells out the word "USED" whenever it becomes visible, i.e., after use, but other words, patterns or symbols could be presented. Ink pattern 20 could be on the bottom side of protective barrier 12 or on both sides.

In FIG. 1B, indicator marks 22 are printed at the head and foot ends of the bottom side of protective barrier 12. Indicator marks 22 may be arrows or other geometric designs which are adapted to be lined up with registration marks on the patient transfer device. The main function of indicator marks 22 is to ensure the correct installation and alignment of disposable comfort sheet 10. Instructions 24 may be printed along one of the sides of protective barrier 12 so they will be upright and readable from the perspective of the operator as disposable comfort sheet 10 is installed on the patient transfer device.

Adhesive strips 14 are further explained with reference to FIG. 2 which illustrates a modified version 10' of the disposable comfort sheet constructed in accordance with the present invention. Disposable comfort sheet 10' is essentially identical to disposable comfort sheet 10 of FIG. 1A, 1B, except that disposable comfort sheet 10' has an optional peel-away layer 30 that is discussed further below.

Two double-sided adhesive strips 14 are affixed along the longitudinal edges of the bottom side of protective barrier 12. A given adhesive strip 14 may take the form of a pressure-sensitive tape (PST) having a dual layer adhesive including a weaker pressure-sensitive adhesive (PSA) 32 and a stronger PSA 34. The adjectives "weaker" and "stronger" here are relative, meaning that the adhesive strength of the stronger PSA 34 is significantly higher than the adhesive strength of the weaker PSA 32, and should not be construed in absolute terms. Weaker PSA 32 is the adhesive which will be in direct contact with the upper belt of the patient transfer device. Stronger PSA 34 adheres to protective barrier 12. A removable liner 36 covers and protects the exposed adhesive on the double sided adhesive strips, and is removed and discarded at the time of use of disposable comfort sheet 10.

These double-sided adhesive strips are used to adhere the comfort sheet to the upper belt of the patient transfer device, and cause the comfort sheet to move with the patient transfer device belts. Thus as the patient transfer support system belts move under the patient during the acquisition process, the comfort sheet (adhered to the upper belt through the adhesive strips) prevents the patient's skin from directly contacting the belt, and also absorbs fluids produced by the patient. As the patient is discharged onto another support surface, the support system belts are withdrawn from underneath the patient. Since the comfort sheet is still adhered to and held in contact with the upper belt by the adhesive strips, it also moves out from under the patient, and is then ready to be removed from the patient transfer device.

After a single use, the comfort sheet is removed from the upper patient transfer system belt by peeling the adhesive strips from the belt. This action is most easily accomplished by grasping and pulling the non-adhered adjacent edge of the comfort sheet in the lengthwise direction of the adhesive strip on the comfort sheet. This motion causes the adhesive bond between the adhesive strip and the belt to be placed in a peeling mode which in turn causes the adhesive bond between the comfort sheet and the belt to be broken. Through proper selection of the adhesions and internal tear strengths of the materials used in the PST and comfort sheet, the adhesive strips can be cleanly removed from the belt, leaving practically no adhesive residue on the belt.

For the adhesive bond between the upper belt surface and the adhesive strip to remove cleanly, none of the other layers or bonds between layers in the tape or comfort sheet can fail under the peeling forces generated during removal of the used comfort sheet from the patient transfer device. In other words, the internal strengths of all layers and the bonds between layers are most desirably higher in a peeling mode than the final bond between the outside layer of the double-sided tape and the upper patient transfer device belt. The following list identifies the layers, internal strengths, and bonds between layers which provide the cleanest removal of the adhesive strip from the upper patient transfer device belt: (i) the internal strength of the absorbent layer should be greater than the peel adhesion of the double-sided adhesive strip to the belt; (ii) the bond between the absorbent layer and the waterproof layer should be greater than the peel adhesion of the double-sided adhesive strip to the belt; (iii) the internal strength of the waterproof layer should be greater than the peel adhesion of the double-sided adhesive strip to the belt; (iv) the bond between the waterproof layer and the first adhesive layer on the first side of the adhesive strip should be greater than the peel adhesion of the double sided adhesive strip to the belt; (v) the internal strength of the first adhesive layer should be greater than peel adhesion of the double-sided adhesive strip to the belt; (vi) the bond between the first adhesive layer and the second adhesive layer should be greater than the peel adhesion of the double-sided adhesive strip to the belt (or the bond between the first adhesive layer and an intermediate film carrier located between the first and second adhesive layers should be greater than the peel adhesion of the double-sided adhesive strip to the belt, the internal strength of the film carrier should be greater than the peel adhesion of the double-sided adhesive strip to the belt, and the bond between the film carrier and the second adhesive layer should be greater than the peel adhesion of the double-sided adhesive strip to the belt); and (vii) the internal strength of the second adhesive layer should be greater than the peel adhesion of the double-sided adhesive strip to the belt. The bond between the second adhesive layer and the upper belt of the patient transfer device thereby separates cleanly from the belt when a peeling force is applied to the adhesive strips by pulling up the edges of the comfort sheet.

It may also be advantageous to apply PSA-coated, single-sided tape strips (not shown) to each end of adhesive strips 14. The single-sided tape strips are about as wide as adhesive strips 14. With protective liner 36 on adhesive strips 14 pulled back approximately 2" from each end of adhesive strips 14, the single-sided tape strips would be applied approximately 1" from each end of an adhesive strip 14. Once applied, the single-sided tape strips extend beyond the end of comfort sheet 10. They would then be folded over the edge of the comfort sheet and adhered to the top side of the comfort sheet with their own adhesive. The purpose of these single-sided tape strips is to prevent delamination of the double-sided tape or layers in the comfort sheet at the edges of the sheet and at the ends of the adhesive strips.

Although the bond between the belt and the application side of the double-sided adhesive strip may allow for clean removal from the belt, it and all of the other layers in the comfort sheet should have sufficient strength in a shear mode to prevent the comfort sheet from tearing as the upper belt moves under the patient during the patient acquisition process.

Figure 2:
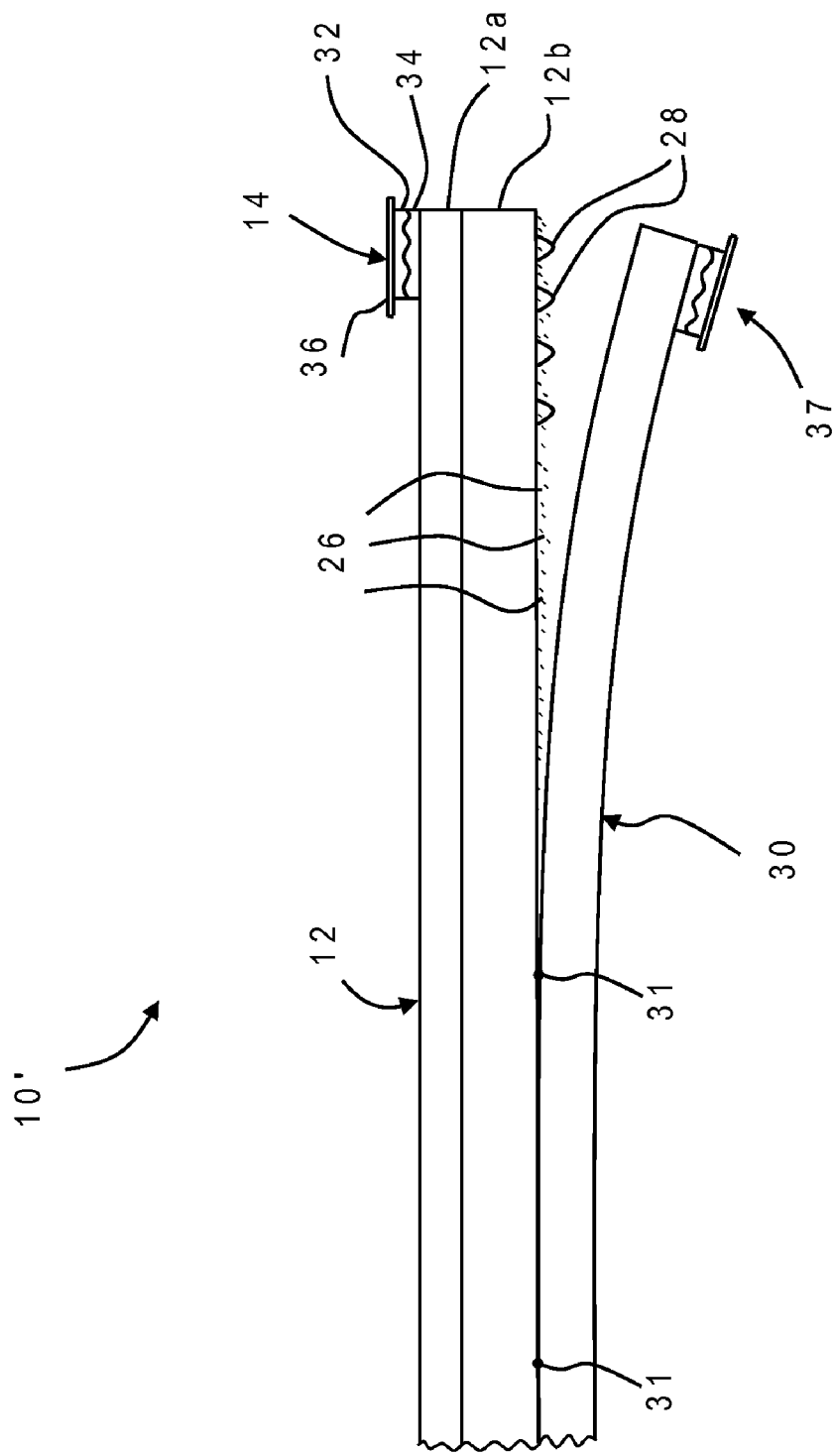
FIG. 2 is an edge view of another embodiment of a disposable comfort sheet constructed in accordance with the present invention illustrating a bottom peel-away layer and sections of the adhesive strips.

FIG. 2 also illustrates a preferred layered construction for protective barrier 12. Protective barrier 12 is comprised of at least two layers, a waterproof layer 12a and an absorbent layer 12b. Waterproof layer 12a will be in contact with the upper belt of the patient transfer device, and prevents the transmission of fluids or other contaminants (e.g., skin flakes) to upper belt 40. Adhesive strips 14 are thus affixed to waterproof layer 12a. Absorbent layer 12b will be in contact with the patient, and advantageously has other properties such as providing a soft feel and lifting against the patient's skin or clothing. Waterproof layer 12a can be permanently and directly bonded thermally or adhesively to absorbent layer 12b, and the bond is preferably continuous without interruptions or discontinuities. In an alternative embodiment waterproof layer 12a is a vapor barrier film or coating applied to absorbent layer 12b.

In the enhanced disposable comfort sheet 10', an optional peel-away layer 30 is further releasably attached to absorbent layer 12b. Peel-away layer 30 also has adhesive strips 37 affixed along its longitudinal edges. Adhesive strips 37 preferably have the same dual adhesive construction as adhesive strips 14. While protective barrier 12 is adapted to surround and protect the upper belt of the patient transfer device, peel-away layer 30 is adapted to surround and protect the lower belt of the device as explained further below in conjunction with FIGS. 4A-4F. Peel-away layer 30 is preferably seamless and waterproof, and may be releasably attached to protective barrier 12 by any convenient means such as adhesive drops or spot welding (thermal or sonic) 31 spread substantially across the entire area of disposable comfort sheet 10', which temporarily bonds points of peel-away layer 30 to absorbent layer 12b for example in a grid pattern with a spacing of around 0.5"×0.5".

The top surface of protective barrier 12 (i.e., absorbent layer 12b) may further be coated with antimicrobial agents 26. Antimicrobial agents 26 may alternatively be blended with the material forming absorbent layer 12b. The antimicrobial agent is preferably a bactericide approved for contact with human skin. Materials such as zinc or selenium can prevent or reduce the growth and transmission of microorganisms including bacteria. The top surface of protective barrier 12 may also have a series of small bumps, bubbles, ridges, or other protuberances 28 formed near the left and right side edges and extending the length of sheet 10 to assist in initially gripping the patient during acquisition by the patient transfer device.

The "top" side of protective barrier 12 in this embodiment 10' of the disposable comfort sheet is actually covered by peel-away layer 30, so the terms "top" and "bottom" sides should again not be construed in a limiting sense as these terms are only used relative to protective barrier 12. The "left" and "right" sides are similarly used only in a relative sense as the patient may be in different orientations as well as face down (prone) or face up (supine)

The preferred embodiment of the present invention is made of materials and has measurements which will be described in detail below. However, these materials and measurements could be variable, and these values are only considered approximate. For example, the dimensions of the sheet may be different given patients of different sizes or patient transfer devices of different sizes. Also, it might be the case that disposable comfort sheet 10 is composed of other materials because patients have an allergic reaction to the preferred materials. These examples are only illustrations of the fact that the measurements and materials mentioned below are preferred, not required.

In an illustrative embodiment, the overall size of disposable comfort sheet 10 in unfolded position and designed to fit a 500 lb. capacity patient transfer device is 42" wide (W) by 75" long (L). Disposable comfort sheet 10 has a thickness of 0.020". Absorbent layer 12b is preferably a nonwoven polymer such as spun polyester. Vapor barrier layer 12a material is also preferably a polymer such as polyurethane which provides a good grip against the upper belt surface. Peel-away layer 30 is likewise preferably a polymer such as polyurethane which also gives good grip when pressed against the lower belt of the patient transfer device. The coefficient of friction for the surface of absorbent layer 12b against the patient's skin, bed linens, hospital gowns, etc., is in the range of 0.4-0.6 and more preferably 0.5 as will be the coefficient of friction for the surface of waterproof layer 12a against the upper belt. The tensile strength (dry or wet (with distilled water)) of disposable comfort sheet 10 is at least 15 pounds per lineal inch of material. One square foot of absorbent layer 12b holds (without releasing when vertically inclined) at least 10 ml of distilled water, with no seams (laminating or splicing) which would allow leakage or reduce tensile strength. A given adhesive strip 14, 30 is 1" to 1.5" wide with the edge of the PST adjacent and parallel to each 75" long edge of protective barrier 12. Removable liner 36 completely covers the weaker adhesive side of the adhesive strip, and preferably overhangs a bit to facilitate gripping. Removable liner 36 may have printed information or instructions, and may be silicone treated. The delamination prevention strips are 2" long.

Adhesive properties of adhesive strip 14 include high general strength, high shear strength, high tack, and high internal strength. Adhesive strip 14 is designed to be removed cleanly from the upper belt so that no visible adhesive residue exists on the upper belt upon tape removal after 3 days of contact at a temperature of 90° Fahrenheit. Weaker PSA 32 is designed specifically for good adhesion to the upper belt, and is also tailored for strong but removable bond and adhesion to the material of the upper belt. A film carrier may be used between weaker PSA 32 and stronger PSA 34 to strongly bond to both weaker PSA 32 and stronger PSA 34. This film carrier ensures that enough force is applied to the weaker PSA 32 to remove it cleanly from the upper belt, even in the case where protective barrier 12 has been torn. Stronger PSA 34 is an acrylate adhesive with a layer thickness of 0.002" to 0.004". The film carrier is polyester 0.001" to 0.002" thick. Weaker PSA 32 is an acrylate adhesive with a layer thickness of 0.001" to 0.003". The adhesion to upper belt 40 in shear mode is preferably at least 15 pounds per lineal inch of adhesive in contact with the upper belt. The adhesion to the upper belt in peel mode is preferably at least 3 pounds per lineal inch of width of adhesive in contact with the upper belt. The shear strength of the adhesive strips are preferably at least 30 pounds per square inch.

The following is a recommended manufacturing process for disposable comfort sheet 10. A backing web (consisting of absorbent layer 12b and vapor barrier film 12a) is unrolled from a 42" wide jumbo roll with the web traveling in lengthwise direction of disposable comfort sheet 10. Crowned rollers are used to stretch the web in the width-wise direction to remove wrinkles and bring edges of the web against edge guides to locate the edges for lamination of the PST. The double-sided tape webs are then unrolled from level wound 6,000 yard rolls aligned to each edge of the web, and guided into the nip of a laminating roller set at each edge of the web. The double-sided PST is laminated to the web with removable liner 36 in place, and is press bonded to the web with nip rollers. The web with the PST bonded in place is continuously folded in width-wise direction to 10.5 inch width (three folds) and the web folds are pressed flat. The partially folded web with PST bonded in place is cut into 75" lengths, and refolded cross-web with five folds to 12.5 inch length. The folded disposable comfort sheet 10 with PST applied may be placed into printed plastic bags, with instructions for use printed on bag. Disposable comfort sheet 10 may optionally be sterilized before final packaging.

The four delamination prevention tape strips (if used) can be applied after the comfort sheets are cut to length, folded along their length, and separated for access to the ends of the sheet (opposite the sides with the double-sided adhesive strips), but before the sheets are folded cross-wise and placed in plastic bags. The delamination prevention tape strips would be applied, after the liners have been manually pulled back to expose approximately two inches of the double-sided adhesive strips, to the exposed adhesive layer of the double-sided adhesive strips with one inch overhanging each end of the doubles-sided strips. The remaining one inch of the delamination prevention tape strips would be folded over and adhered to the back side of the comfort sheet on each corner. The liner can then be reattached to the double-sided adhesive strips, after which the comfort sheet would be cross-folded and placed in its plastic packaging.

Figure 3:
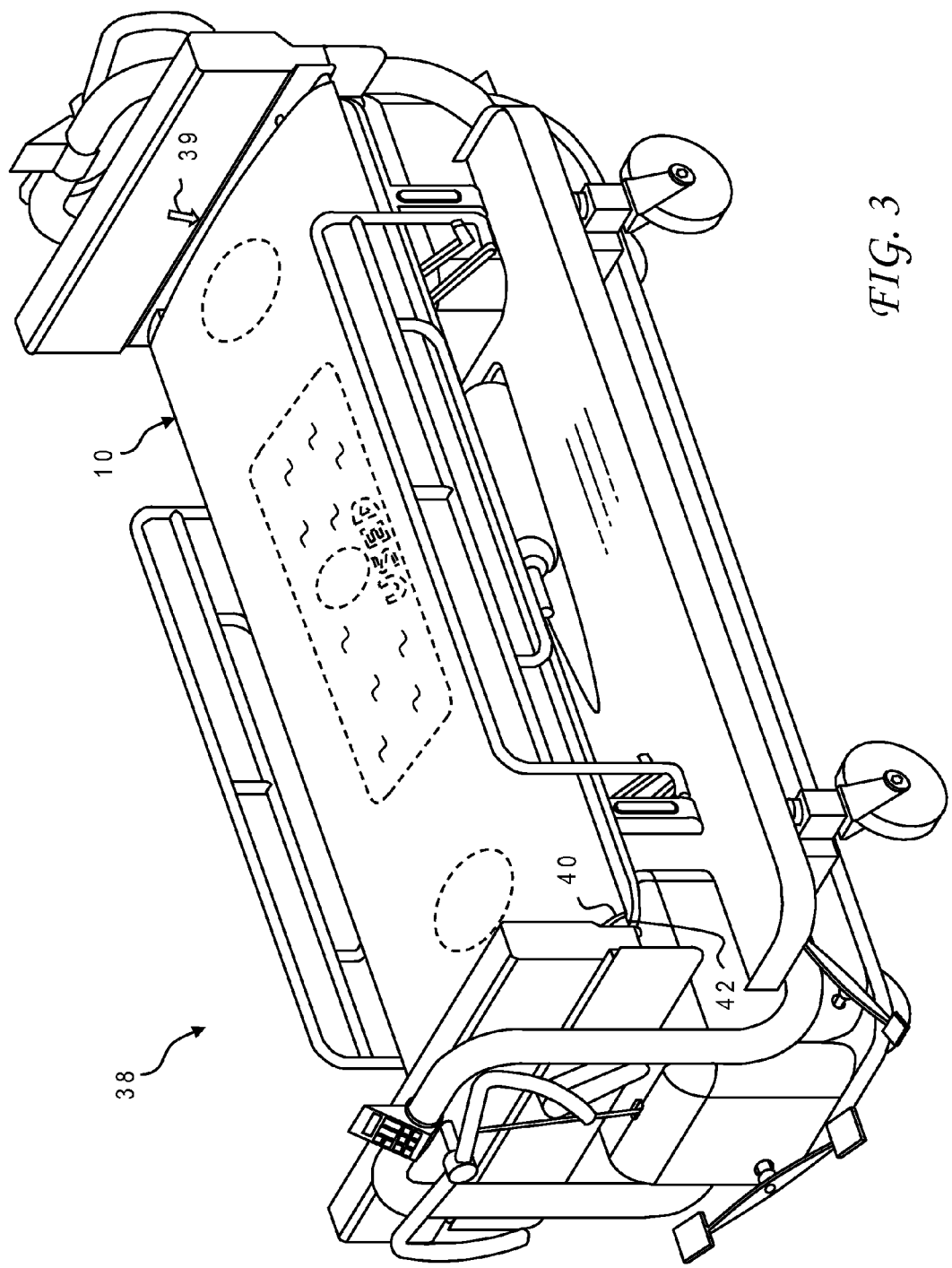
FIG. 3 is a perspective view of a conventional patient lift and transfer device with the disposable comfort sheet of FIG. 1A attached to the upper belt and moved to a position on top of the upper belt.

With further reference to FIG. 3, disposable comfort sheet 10 is shown deployed on the upper belt table of a patient transfer device 38. Patient transfer device 38 has counter-rotating upper and lower belts which can be used to transport a patient laterally from one support surface to another, such as from a hospital bed to an examination table. In this representation, disposable comfort sheet 10 has been attached to the upper belt which has been rotated around so that the top side of disposable comfort sheet 10 is visible (i.e., the side having the heat- or moisture-sensitive ink pattern). One of the registration marks 39 is visible which is used to align indicator marks 22 printed on the bottom side of sheet 10. Disposable comfort sheet 10 can be provided in either sealed plastic bags or in roll form and, if provided in roll form, the roll can be stored under the belt tables of patient transfer device 38. For more details regarding the specific construction of patient transfer device 38, see U.S. Pat. No. 7,540,044. Those skilled in the art will appreciate that the reference to this specific patient transfer device 38 is exemplary only, and that various embodiments of the disposable comfort sheet of the present invention may be installed and used on other patient transfer devices having at least one rotating belt.

Figure 4A:
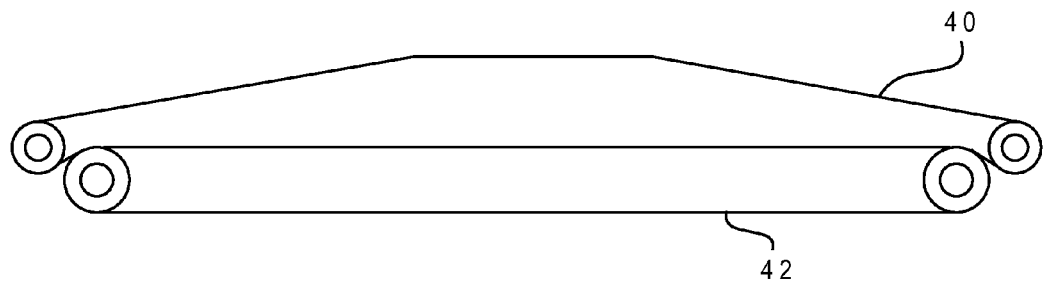

FIGS. 4A-4F illustrate the steps involved in installing enhanced disposable comfort sheet 10' onto the belts of patient transfer device 38. FIG. 4A shows a side view of the counter-rotating upper and lower belts 40, 42 in a closed position wherein upper belt 40 is in contact with lower belt 42, and both belt tables are generally parallel to one another. Patient transfer device 38 might typically be stored in this closed position.

Figure 4D:
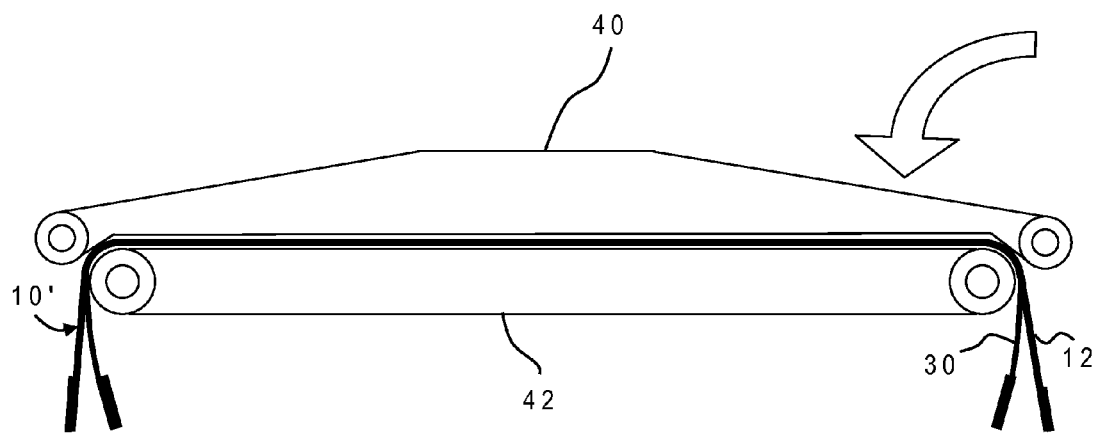
Figure 4B:
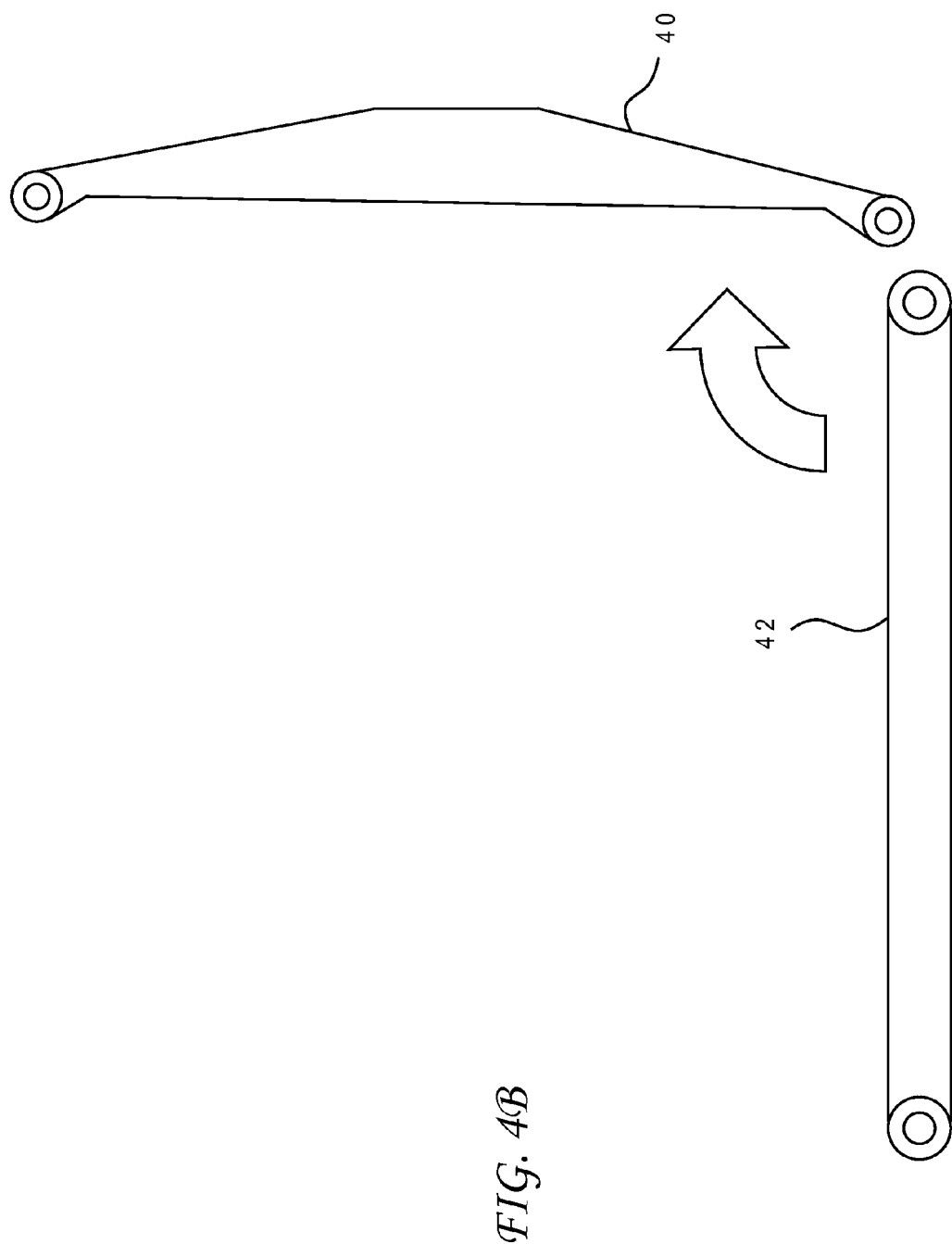

In FIG. 4B, the counter-rotating belts are now in an open position characterized by pivoting upper belt 40 upwardly (clockwise in this view) so that the upper belt table and the lower belt table are generally perpendicular to one another. In the open position the surfaces of the belts are no longer touching each other, and there is sufficient space between the belts to insert a disposable comfort sheet. If patient transfer device 38 was previously cleaned and left with the belt tables in the open position, then the installation of the disposable comfort sheet skips the step from FIG. 4A to 4B.

In FIG. 4C, disposable comfort sheet 10' has been placed on top of the upper surface of lower belt 42 by a nurse or other medical professional. In this implementation, the separable layer 30 is in direct contact with lower belt 42, while the protective barrier 12 is not in direct contact since it is attached to the side of optional peel-away layer 30 which is opposite the side in contact with lower belt 42. If optional peel-away layer 30 were not present (i.e., using disposable comfort sheet 10 of FIGS. 1A, 1B), then protective barrier 12 would be in direct contact with lower belt 42. The sides of both protective barrier 12 and separable layer 30 are hanging off the sides of lower belt 42. Adhesive strips 37 are located on the side of optional peel-away layer 30 which faces inward towards lower belt 42. Adhesive strips 14 are located on the side of the protective barrier 12 which is facing outward from lower belt 42.

In FIG. 4D the upper belt table of patient transfer device 38 has been moved back to the closed position by pivoting it counter-clockwise. Disposable comfort sheet 10' is forcibly captured between the upper belt 40 and lower belt 42 with the sides still hanging down.

Figure 4E:
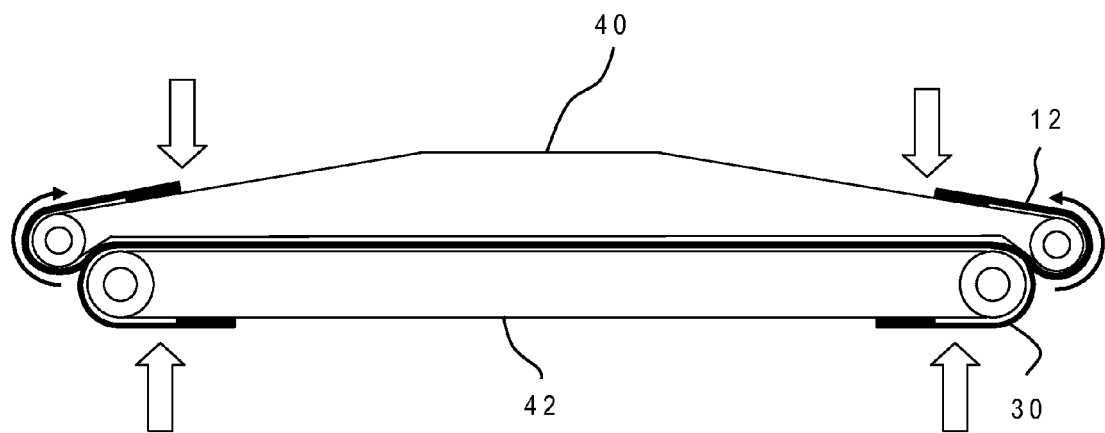

In FIG. 4E, the sides of protective barrier 12 and peel-away layer 30 are no longer dangling freely from the sides of lower belt 42 as in FIGS. 4C and 4D. The operator wraps the sides of protective barrier 12 around the sides of upper belt 40, and removes liners 36 from adhesive strips 14. Adhesive strips 14 are then applied to upper belt 40 by pressing the PST firmly against the belt along the lengths of the strips, with protective barrier 12 being maintained taut and preferably wrinkle-free, to secure the sides of protective barrier to the top surface of upper belt 40 proximate each side edge thereof. In this manner whenever upper belt 40 rotates, protective barrier 12 will rotate along with it with essentially no slippage. The operator similarly wraps the sides of peel-away layer 30 around the sides of lower belt 42, and removes liners 36 from adhesive strips 37. Adhesive strips 37 are then applied to lower belt 40 by pressing the PST firmly against the belt along the lengths of the strips, with peel-away layer 30 being maintained taut and preferably wrinkle-free. In this manner whenever lower belt 40 rotates, peel-away layer 30 will rotate along with it with essentially no slippage.

Figure 4F:
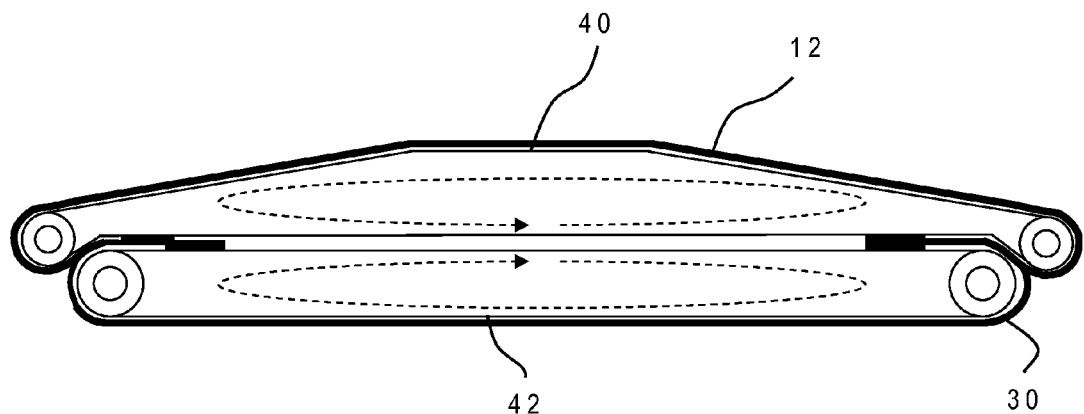

One potential realization of the different configurations which can be created by rotation of the belts is exemplified in FIG. 4F. Upper belt 40 has rotated counter-clockwise in this view and lower belt 42 has rotated clockwise, for "friction-less" engagement while acquiring the patient. As the two belts counter-rotate, peel-away layer 30 progressively separates along most of its width from protective barrier 12, with protective barrier 12 covering the entire top surface of upper belt 40 while peel-away layer 30 stays attached to lower belt 42. Upper belt 40 is thereby protected from contamination by the patient.

After the patient has been delivered, protective barrier 12 and peel-away layer 30 will again be in the configuration shown in FIG. 4E, so any contaminants that may be retained on absorbent layer 12b are prevented from contacting lower belt 42 by peel-away layer 30. The operator may thereafter pull the adhesive strips off their respective belts so the sides of protective barrier 12 and peel-away layer 30 are again hanging as seen in FIG. 4D, and then move the belt tables to the open position shown in FIG. 4C to remove and discard protective barrier 12 and peel-away layer 30.

While the foregoing description refers to the enhanced embodiment 10' of the disposable comfort sheet of the present invention, significant benefits may still be obtained by using only protective barrier 12 in the same manner illustrated in FIGS. 4A-4F but without peel-away layer 30. In other embodiments of the present invention the disposable comfort sheet may have additional layers, films or coatings applied to one or both of protective barrier 12 and peel-away layer 30.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. It is therefore contemplated that such modifications can be made without departing from the spirit or scope of the present invention as defined in the appended claims.

What is claimed is:

1. An article comprising a generally rectangular sheet having a seamless, waterproof layer and an absorbent layer; a first longitudinal adhesive strip applied to said waterproof layer along a first side edge thereof; and a second longitudinal adhesive strip applied to said waterproof layer along a second side edge thereof, opposite said first side edge, wherein each of said first and second adhesive strips has duel adhesive layers including a first adhesive bond to said waterproof layer and a second adhesive applied to said first adhesive; and an adhesive strength of said first adhesive is higher than an adhesive strength of said second adhesive.

2. The article of claim 1 wherein said absorbent layer is directly bonded to said waterproof layer.

3. The article of claim 1 wherein said absorbent layer includes a section having additional absorbency to retain higher amounts of fluids than the remainder of said absorbent layer.

4. The article of claim 1 wherein said article is adapted for use with a patient transfer device having registration marks for installation of the article, and further comprising indicator marks printed at predetermined locations on an outer surface of said waterproof layer for alignment with the registration marks.

5. The article of claim 1 wherein:
    said waterproof layer is a bottom layer whose outer surface has a coefficient of friction of at least 0.5; and
    said absorbent layer is a top layer whose outer surface has a coefficient of friction of at least 0.5.

6. The article of claim 1, further comprising an antimicrobial agent applied to said absorbent layer.

7. A disposable comfort sheet for use with a patient transfer device, comprising:
    a generally rectangular sheet-like barrier having an absorbent layer, a seamless waterproof layer permanently bonded to a first side of said absorbent layer, and a peel-away layer releasably bonded to a second side of said absorbent layer opposite said first side;
    first and second longitudinal adhesive strips applied to an outer surface of said waterproof layer along first and second side edges thereof; and
    third and fourth longitudinal adhesive strips applied to an outer surface of said peel-away layer along first and second side edges thereof.

8. The disposable comfort sheet of claim 7 wherein said peel-away layer is also waterproof.

9. The disposable comfort sheet of claim 7 wherein said peel-away layer is releasably bonded to said absorbent layer by spot welding spread substantially across the entire area of said barrier.

10. A method of installing a disposable comfort sheet onto a patient transfer device having upper and lower counter-rotating belts, comprising:
    moving the upper belt away from the lower belt to an open position;
    placing the disposable comfort sheet on top of the lower belt with a first side of the disposable comfort sheet hanging off a first side edge of the lower belt and a second side of the disposable comfort sheet opposite the first side hanging off a second side edge of the lower belt opposite the first side edge;
    moving the upper belt from the open position to a closed position wherein the disposable comfort sheet is forcibly captured between the upper and lower belts;
    wrapping the first side of the disposable comfort sheet around a first side edge of the upper belt and securing the first side to a top surface of the upper belt proximate the first side edge thereof; and
    wrapping the second side of the disposable comfort sheet around a second side edge of the upper belt and securing the second side to the top surface of the upper belt proximate the second side edge thereof.

11. The method of claim 10 wherein the disposable comfort sheet has a first pressure-sensitive adhesive strip affixed longitudinally to the first side thereof and a second pressure-sensitive adhesive strip affixed longitudinally to the second side thereof, and the first and second sides of the disposable comfort sheet are secured by pressing the first and second pressure-sensitive adhesive strips against the top surface of the upper belt.

12. The method of claim 10, further comprising aligning one or more indicator marks on the disposable comfort sheet with one or more registration marks on the patient transfer device while placing the disposable comfort sheet on top of the lower belt.

13. The method of claim 10 wherein the disposable comfort sheet includes a separable layer which is in contact with the lower belt after said placing with a first side of the separable layer hanging off the first side edge of the lower belt and a second side of the separable layer opposite the first side hanging off the second side edge of the lower belt, and further comprising:
    wrapping the first side of the separable layer around the first side edge of the lower belt and securing the first side of the separable layer to a bottom surface of the lower belt proximate the first side edge thereof and
    wrapping the second side of the separable layer around the second side edge of the lower belt and securing the second side of the separable layer to the bottom surface of the lower belt proximate the second side edge thereof.

14. The method of claim 13 wherein the separable layer is releasably bonded to a barrier layer of the disposable comfort sheet, and further comprising counter-rotating the upper and lower belts while acquiring a patient such that the separable layer progressively separates along its width from the barrier layer.

15. An article comprising: a generally rectangular sheet having a seamless, waterproof layer and an absorbent layer; a first longitudinal adhesive strip applied to said waterproof layer along a first side edge thereof; and
    a second longitudinal adhesive strip applied to said waterproof layer along a second side edge thereof, opposite said first side edge,
    wherein said absorbent layer includes a section having additional absorbency to retain higher amounts of fluids than the remainder of said absorbent layer.

16. An article comprising: a generally rectangular sheet having a seamless, waterproof layer and an absorbent layer; a first longitudinal adhesive strip applied to said waterproof layer along a first side edge thereof; and
    a second longitudinal adhesive strip applied to said waterproof layer along a second side edge thereof, opposite said first side edge,
    wherein said article is adapted for use with a patient transfer device having registration marks for installation of the article, and further comprising indicator marks printed at predetermined locations on an outer surface of said waterproof layer for alignment with the registration marks.

* * * * *